(12) United States Patent
Cavallazzi et al.

(10) Patent No.: US 7,722,611 B2
(45) Date of Patent: May 25, 2010

(54) METHOD OF TREATING A CLAVICLE FRACTURE

(75) Inventors: Cesare Cavallazzi, Miramar, FL (US); Joel Marquart, Pembroke Pines, FL (US); Marcus Bourda, Miami, FL (US); Javier E. Castaneda, Miami, FL (US)

(73) Assignee: Depuy Products, Inc., Warsaw, IN (US)

( * ) Notice: Subject to any disclaimer, the term of this patent is extended or adjusted under 35 U.S.C. 154(b) by 463 days.

(21) Appl. No.: 11/682,210

(22) Filed: Mar. 5, 2007

(65) Prior Publication Data

US 2008/0221574 A1 Sep. 11, 2008

(51) Int. Cl.
    *A61B 17/58* (2006.01)
(52) U.S. Cl. .................. 606/62; 606/60; 623/16.11
(58) Field of Classification Search ............. 606/60–64, 606/280, 54, 57, 69, 72–73, 286, 289; 623/16.11
    See application file for complete search history.

(56) References Cited

U.S. PATENT DOCUMENTS

| | | | |
|---|---|---|---|
| 3,025,853 A | 3/1962 | Mason |
| 3,709,218 A | 1/1973 | Halloran |
| 3,741,205 A | 6/1973 | Markolf et al. |
| 3,939,498 A | 2/1976 | Lee et al. |
| 4,119,092 A | 10/1978 | Gil |
| 4,135,507 A | 1/1979 | Harris |
| 4,153,953 A | 5/1979 | Grobbelaar |
| 4,172,452 A | 10/1979 | Forte et al. |
| 4,483,335 A | 11/1984 | Tornier |
| 4,506,662 A | 3/1985 | Anapliotis |
| 4,565,193 A | 1/1986 | Streli |
| 4,733,654 A | 3/1988 | Marino |
| 4,776,330 A | 10/1988 | Chapman et al. |
| 4,794,919 A | 1/1989 | Nilsson |
| 4,923,471 A | 5/1990 | Morgan |
| 5,013,314 A | 5/1991 | Firica et al. |
| 5,035,697 A | 7/1991 | Frigg |

(Continued)

FOREIGN PATENT DOCUMENTS

EP 0451427 A1 5/1990

OTHER PUBLICATIONS

Rockwood Clavicle Pin, Design Rationale and Surgical Technique, DePuy International Ltd., Nov. 2005.

*Primary Examiner*—Eduardo C Robert
*Assistant Examiner*—Christina Negrelli
(74) *Attorney, Agent, or Firm*—Gordon & Jacobson, PC

(57) ABSTRACT

A method of clavicle fracture fixation includes using a K-wire to create a pilot hole extending longitudinally through the medullary canal of the lateral and medial fragments of the fractured clavicle while the fragments are reduced, enlarging a medial portion of the pilot hole in the lateral fragment and a lateral portion of the pilot hole in the medial fragment, wherein such enlarged portions are together sized for receiving the clavicle nail, attaching the lateral end of the clavicle nail to the K-wire, manipulating the K-wire such that substantially the entire length of the clavicle nail is positioned inside of the lateral fragment, aligning the lateral and medial fragments longitudinally, and manipulating the K-wire such that approximately half of the length of the clavicle nail is positioned within the medial fragment and approximately half of the nail is positioned within the lateral fragment.

20 Claims, 20 Drawing Sheets

U.S. PATENT DOCUMENTS

| | | |
|---|---|---|
| 5,190,544 A | 3/1993 | Chapman et al. |
| 5,201,733 A | 4/1993 | Etheredge, III |
| 5,304,180 A | 4/1994 | Slocum |
| 5,352,229 A | 10/1994 | Goble et al. |
| 5,356,410 A | 10/1994 | Pennig |
| 5,382,248 A | 1/1995 | Jacobson et al. |
| 5,458,654 A | 10/1995 | Tepic |
| 5,472,444 A | 12/1995 | Huebner et al. |
| 5,484,438 A | 1/1996 | Pennig |
| 5,536,127 A | 7/1996 | Pennig |
| 5,578,035 A | 11/1996 | Lin |
| 5,591,168 A | 1/1997 | Judet et al. |
| 5,603,715 A | 2/1997 | Kessler |
| 5,662,655 A | 9/1997 | Laboureau et al. |
| 5,665,086 A | 9/1997 | Itoman et al. |
| 5,665,087 A | 9/1997 | Huebner |
| 5,665,089 A | 9/1997 | Dall et al. |
| 5,676,667 A | 10/1997 | Hausman |
| 5,709,682 A | 1/1998 | Medoff |
| 5,709,686 A | 1/1998 | Talos et al. |
| 5,718,705 A | 2/1998 | Sammarco |
| 5,733,287 A | 3/1998 | Tepic et al. |
| 5,749,872 A | 5/1998 | Kyle et al. |
| 5,766,174 A | 6/1998 | Perry |
| 5,772,662 A | 6/1998 | Chapman et al. |
| 5,776,194 A | 7/1998 | Mikol et al. |
| 5,931,839 A | 8/1999 | Medoff |
| 5,938,664 A | 8/1999 | Winquist et al. |
| 5,967,046 A | 10/1999 | Muller |
| 5,968,046 A | 10/1999 | Castleman |
| 6,010,505 A | 1/2000 | Asche et al. |
| 6,022,350 A | 2/2000 | Ganem |
| 6,146,384 A | 11/2000 | Lee et al. |
| 6,231,576 B1 | 5/2001 | Frigg et al. |
| 6,238,395 B1 | 5/2001 | Bonutti |
| 6,248,109 B1 | 6/2001 | Stoffella |
| 6,270,499 B1 | 8/2001 | Leu et al. |
| 6,355,041 B1 | 3/2002 | Martin |
| 6,379,359 B1 | 4/2002 | Dahners |
| 6,409,768 B1 | 6/2002 | Tepic et al. |
| 6,454,770 B1 * | 9/2002 | Klaue ..................... 606/281 |
| 6,527,775 B1 | 3/2003 | Warburton |
| 6,623,486 B1 | 9/2003 | Weaver et al. |
| 6,645,212 B2 | 11/2003 | Goldhahn et al. |
| 6,706,046 B2 | 3/2004 | Orbay et al. |
| 7,425,213 B2 * | 9/2008 | Orbay ..................... 606/62 |
| 2001/0021851 A1 | 9/2001 | Eberlein et al. |
| 2003/0083661 A1 | 5/2003 | Orbay et al. |
| 2003/0105461 A1 | 6/2003 | Putnam |
| 2004/0102778 A1 | 5/2004 | Huebner et al. |
| 2004/0111090 A1 | 6/2004 | Dahners |
| 2005/0080421 A1 | 4/2005 | Weaver et al. |
| 2006/0015101 A1 | 1/2006 | Warburton et al. |

\* cited by examiner

US 7,722,611 B2

METHOD OF TREATING A CLAVICLE FRACTURE

BACKGROUND OF THE INVENTION

1. Field of the Invention

This invention relates broadly to surgery. Particularly, this invention relates to orthopedic devices for fixation of clavicle fractures and methods of using the same.

2. State of the Art

Traditionally, orthopedic surgeons have accepted nonoperative treatment as the standard of care for fractured clavicles, likely the result of earlier studies showing unsatisfactory outcomes with operative treatment. However, recent studies show significant risks with nonoperative treatment, including chronic pain, weakness, and a higher nonunion rate. Hill, J. M., et al. "Closed Treatment of Displaced Middle-Third Fractures of the Clavicle Gives Poor Results." *Journal of Bone and Joint Surgery*, May 1998: 537-539. In addition, poor operative results in the past may have been related more to the technique used than the concept of treating these fractures operatively.

Placement of plate and screws on the clavicle requires significant soft tissue stripping, which may compromise blood supply to the bone and subsequent healing. Furthermore, this treatment creates multiple stress risers in the clavicle, due to the use of several bicortical screws in the plate. Another treatment, smooth pin fixation, presents problems with possible pin migration.

The Rockwood Clavicle Pin, available from DePuy, fits into the intramedullary canal of the clavicle through a small incision over the fracture site with minimal soft tissue dissection. The device is specially designed to allow natural compression at the fracture site, minimizes hardware migration and can be easily removed under local anesthesia. This pin has a threaded end that may be screwed into the medial fragment of the fractured clavicle. The opposite end has a thread for receiving a nut that may be retained in the lateral fragment and tightened to reduce the fracture. The intramedullary placement of the Rockwood Clavicle Pin helps remedy past treatment issues, including impaired blood supply, painful, prominent hardware, and stress risers related to removal of a plate and associated screws. However, the pin may not be suitable for certain fractures, such as a non-union fracture, where compression across the fracture is undesirable.

The clavicle nail disclosed in co-owned and co-pending U.S. Pub. No. 20050065528 A1 to Orbay, includes threaded parallel holes displaced along an endosteal surface for receiving unicortical machine screws. The surgeon positions the nail inside the medial and lateral fragments of the fractured clavicle and then uses a jig attached to the nail for drilling bone holes in alignment with the threaded screw holes. Screws are inserted through the bone and thread into the nail. The unicortical screws have low-profile heads that tighten against the bone surface while compressing the nail plate against the endosteal wall of the medullary canal to maintain the reduction of the fracture.

Since the time when the application to Orbay was filed, further development has resulted in a nail and implantation method that takes full advantage of proven surgical techniques. In addition, unique structural features have been provided to the new nail that facilitate its implantation within the medullary canal of the clavicle bone and operate to stabilize a clavicle fracture.

SUMMARY OF THE INVENTION

It is therefore an object of the invention to provide a treatment which provides stabilization and support for clavicle fractures.

It is also an object of the invention to provide an intramedullary nail for such treatment.

It is a further object of the invention to provide a nail and treatment for similar fractures.

In accord with these objects, which will be discussed in detail below, an intramedullary nail and method of implanting the same is provided. The nail is an elongate rod including a plurality of threaded holes extending perpendicularly to a lengthwise surface of the rod. Several of the holes include a non-circular socket above the threads at which a jig having a corresponding shape male portion can be rotationally secured, as described below. The ends of the rod are tapered and each includes a threaded bore at which a threaded K-wire can be removably attached.

The method for positioning the clavicle nail inside the intramedullary canal of a fractured bone, such as a clavicle bone, includes (i) creating a pilot hole extending longitudinally through the medullary canal of the lateral and medial fragments of the fractured clavicle while the fragments are held in an approximate healing alignment, (ii) enlarging a medial portion of the pilot hole in the lateral fragment and a lateral portion of the pilot hole in the medial fragment, wherein such enlarged portions are sized for receiving the nail, (iii) attaching the lateral end of the nail to the K-wire, (iv) manipulating the K-wire and nail such that substantially the entire length of the nail is positioned inside of the lateral fragment, (v) aligning the lateral and medial fragments longitudinally, and (vi) manipulating the K-wire and nail such that approximately half of the length of the nail is positioned within the medial fragment and approximately half of the nail is positioned within the lateral fragment.

The method enables implantation of a nail in manner that provides fixation of a fractured clavicle with the advantages of both a pin and a nail; i.e., minimal soft tissue stripping of the clavicle, reduced postoperative pain, and faster healing.

Additional objects and advantages of the invention will become apparent to those skilled in the art upon reference to the detailed description taken in conjunction with the provided figures.

DETAILED DESCRIPTION OF THE PREFERRED EMBODIMENTS

Figure 1:
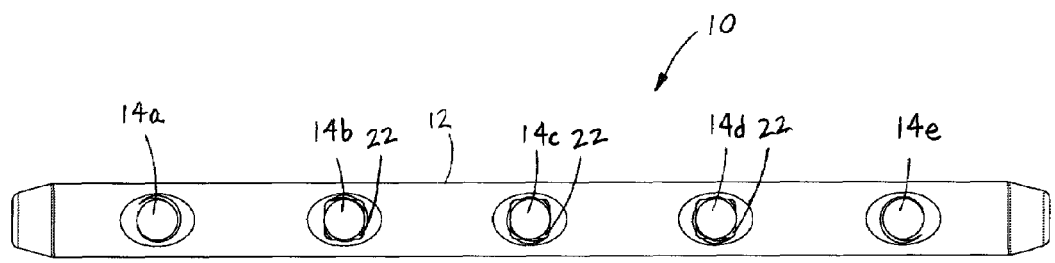
FIG. 1 is a top view of a clavicle nail according to an embodiment of the invention.
Figure 2:
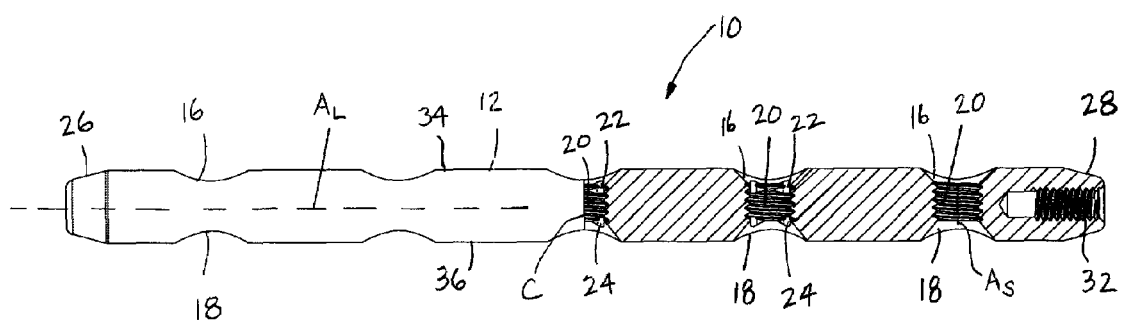
FIG. 2 is a partial section side view of the clavicle nail of FIG. 1.
Figure 3:
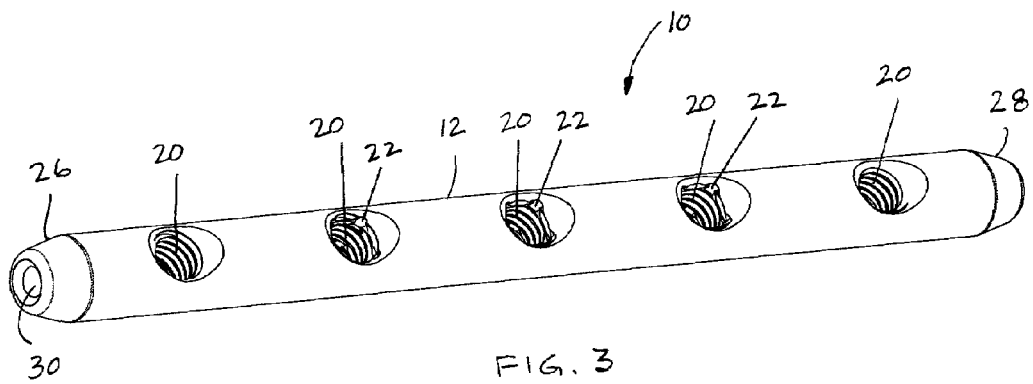
FIG. 3 is a perspective view of the clavicle nail of FIG. 1.

Turning now to FIGS. 1 through 3, a preferred clavicle nail 10 for use according to a preferred application of a preferred system and method of the invention is shown. The nail 10 comprises an elongate rod 12 including five holes 14a, 14b, 14c, 14d, 14e (collectively 14) longitudinally displaced along the rod. The holes 14 extend parallel and perpendicularly through the rod 12. Each hole 14 includes upper and lower recesses 16, 18, and machine threads 20 therebetween for threaded engagement with a screw having a shaft with machine threads. The three central holes 14b, 14c, 14d, referred to as jig holes, each include upper and lower non-circular square sockets 22, 24 between the respective recesses 16, 18 and threads 20. The ends 26, 28 of the rod 12 are tapered and each includes a threaded bore 30, 32 at which a K-wire with a threaded end can be removably attached, as described in more detail below with respect to the method of the invention.

It is noted that the construction of the nail is symmetrical about a plane extending through the longitudinal axis $A_L$ and transverse to the respective axes $A_S$ of the screw holes. Surfaces 34 and 36 can be oriented interchangeably within the medullary canal of the clavicle bone. In addition, the nail is symmetrical about its longitudinal center C. It may be reversed in longitudinal orientation with similar advantages and without disadvantage. As such, the surgeon may use the nail without regard to its longitudinal or diametric orientation, reducing concern of improper implantation and facilitating and expediting the implantation procedure described below.

Figure 4:
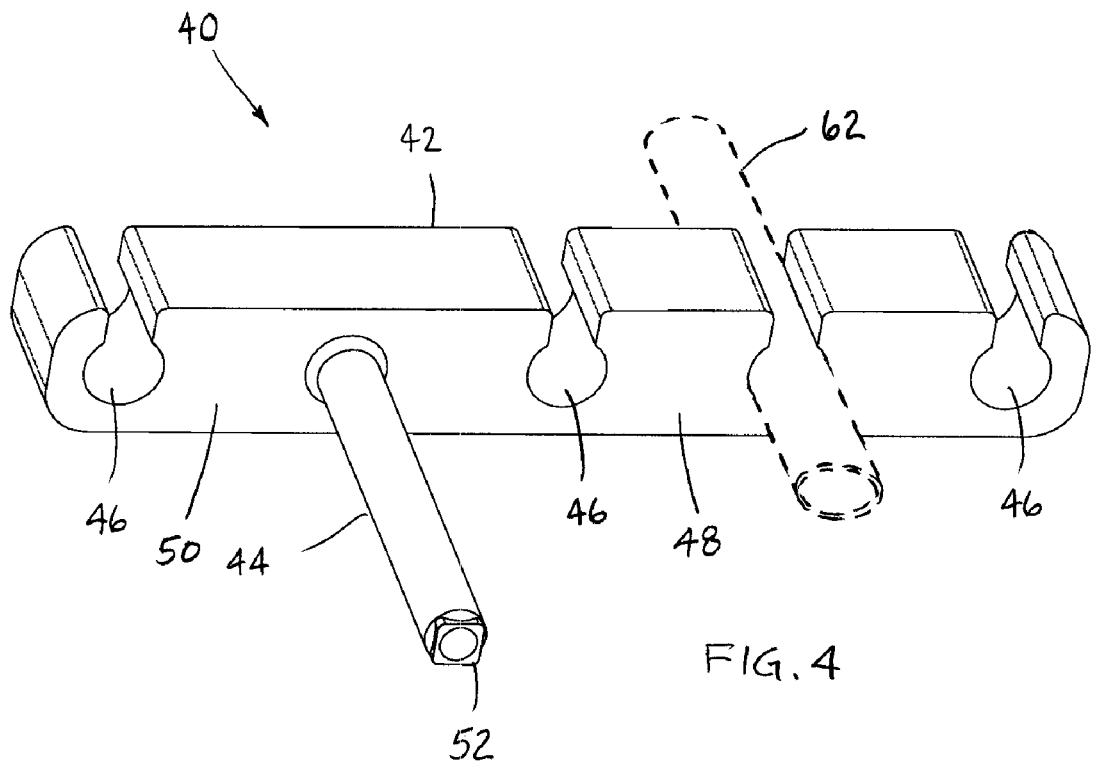
FIG. 4 is a bottom perspective view of a jig used in the method of the invention.
Figure 5:
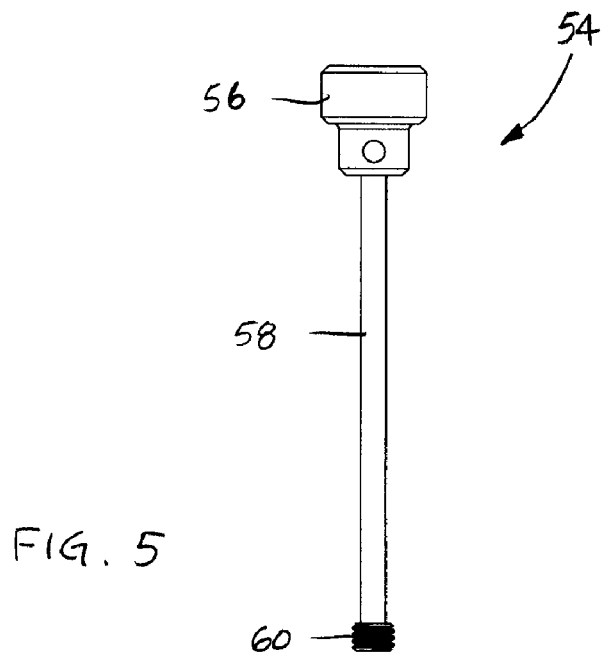
FIG. 5 is a side view of a locking screw for securing the jig of FIG. 4 to the clavicle nail shown in FIGS. 1-3.

Referring to FIG. 4, a jig 40 is provided for attachment to the nail 10 at the jig holes. The jig 40 includes a guide plate 42 and an offset tube 44 extending from a lower side of the plate 42. The guide plate 42 is provided with a plurality of longitudinally displaced guide holes 46 each for receiving a drill guide 62. A longer portion 48 of the guide plate 42 including three guide holes 46 is provided on one side of the offset tube 44 and a shorter portion 50 of the guide plate 42 including one guide hole 46 is provided on the other side of the tube. The tube 44 has a square end 52 sized to be stably received within either of the sockets 22, 24 of the screw holes 14 defined in the nail 10. Referring to FIG. 5, a locking screw 54 is provided to secure the jig 40 at end 48 to the nail 10. The locking screw 54 includes a proximal knob 56 and a shaft 58 with a threaded distal end 60. In operation, the shaft 58 is extended through the offset tube 44 such that the threaded distal end 60 threadably engages a respective screw hole when knob 56 is rotated. Such rotation causes the jig 40 to be compressed between the knob 56 of the locking screw 54 and the nail 10 to lock the jig and nail together.

Figure 6:
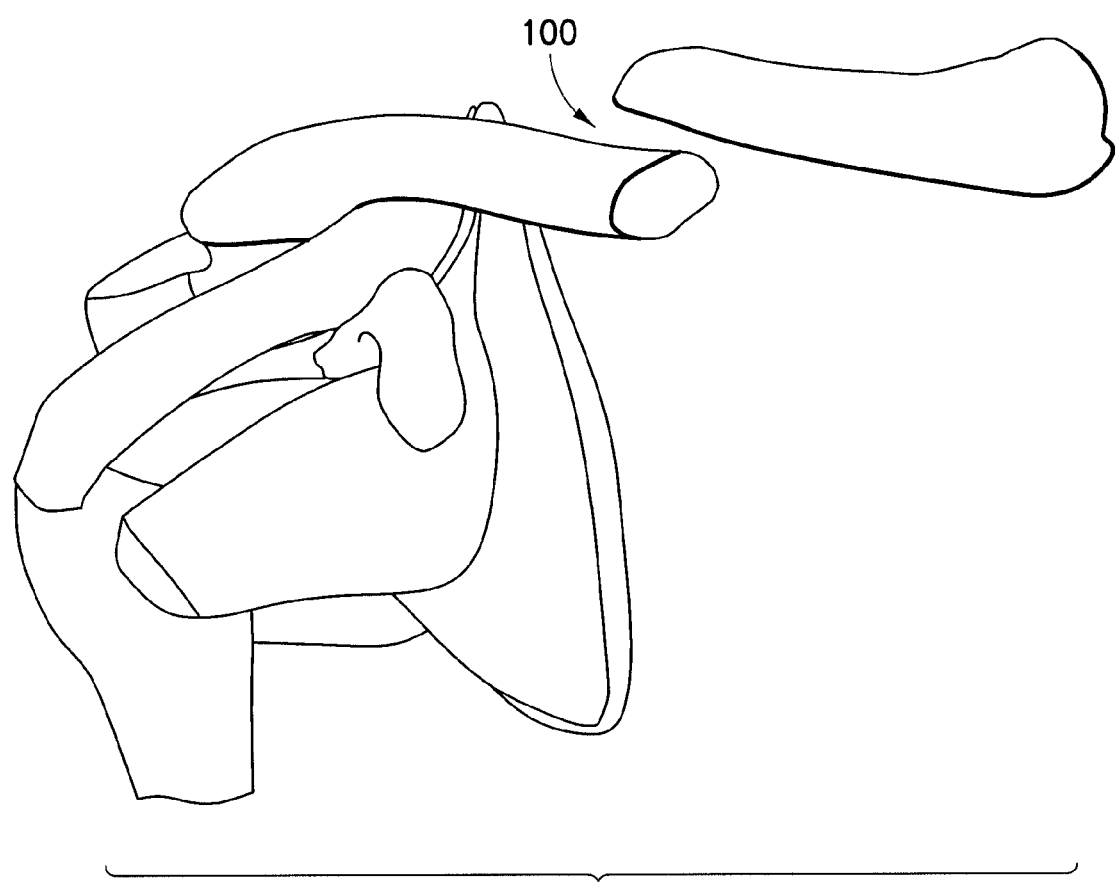
FIGS. 6-23 illustrate a method of implanting a clavicle nail according to the invention.
Figure 7:
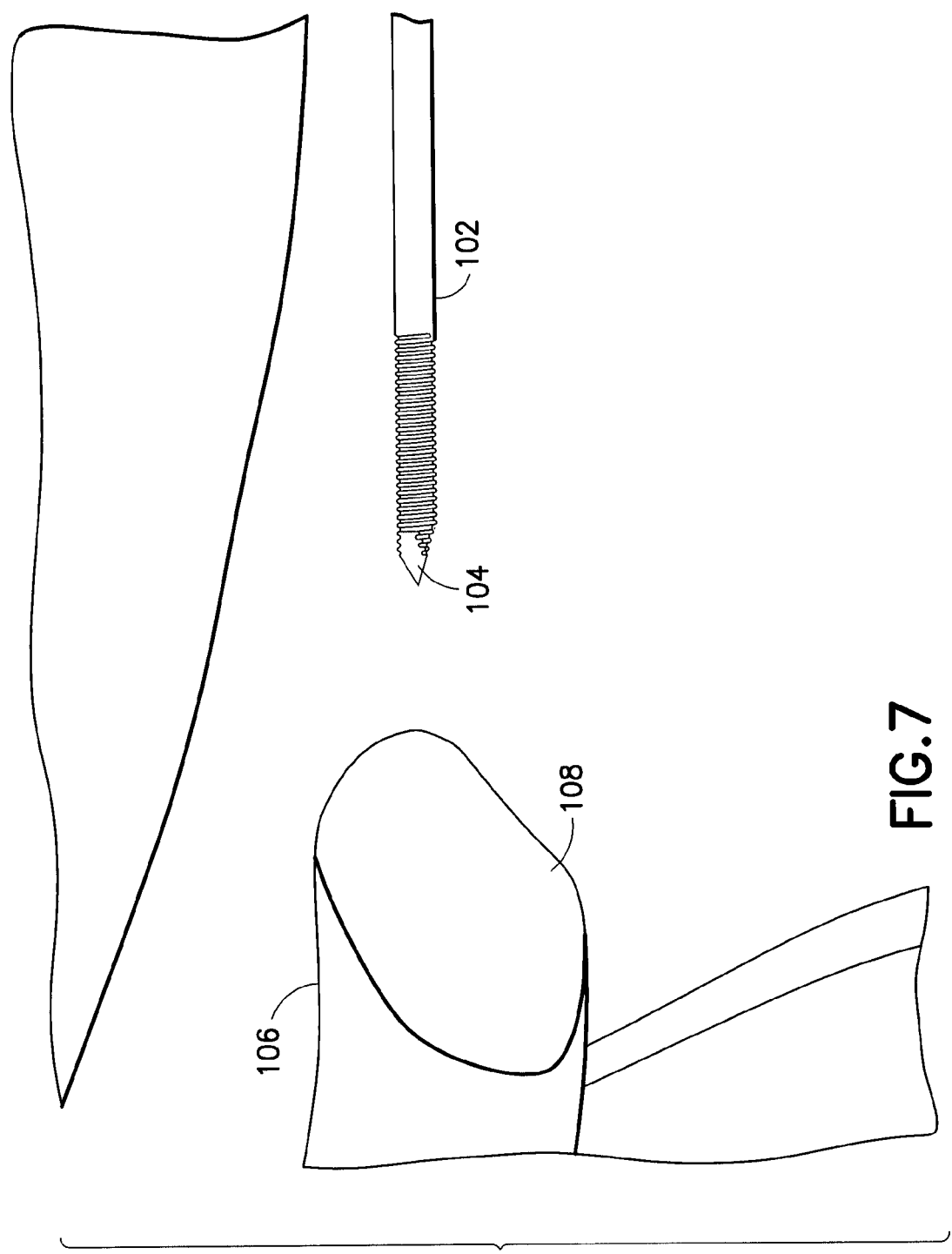
Figure 8:
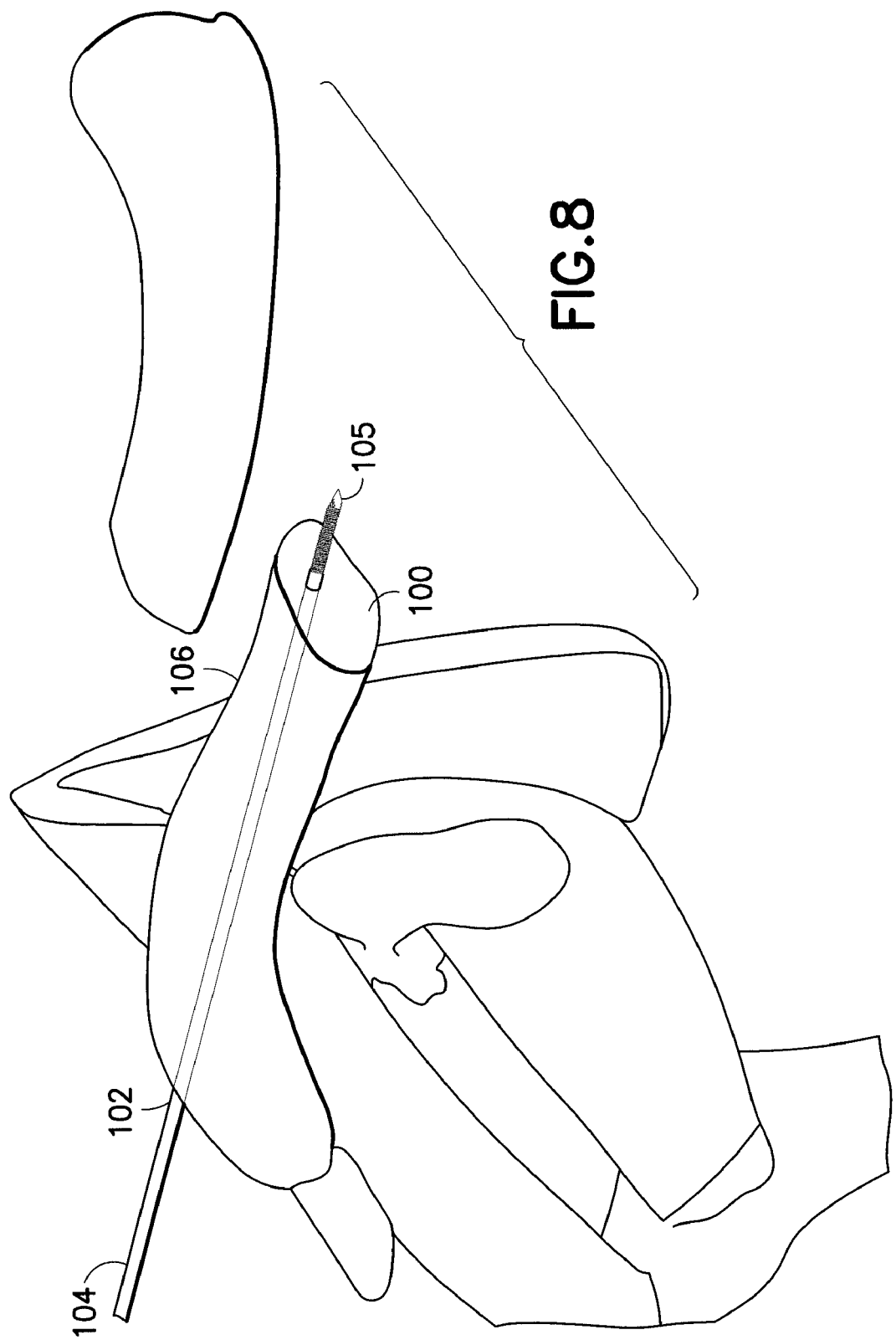
Figure 9:
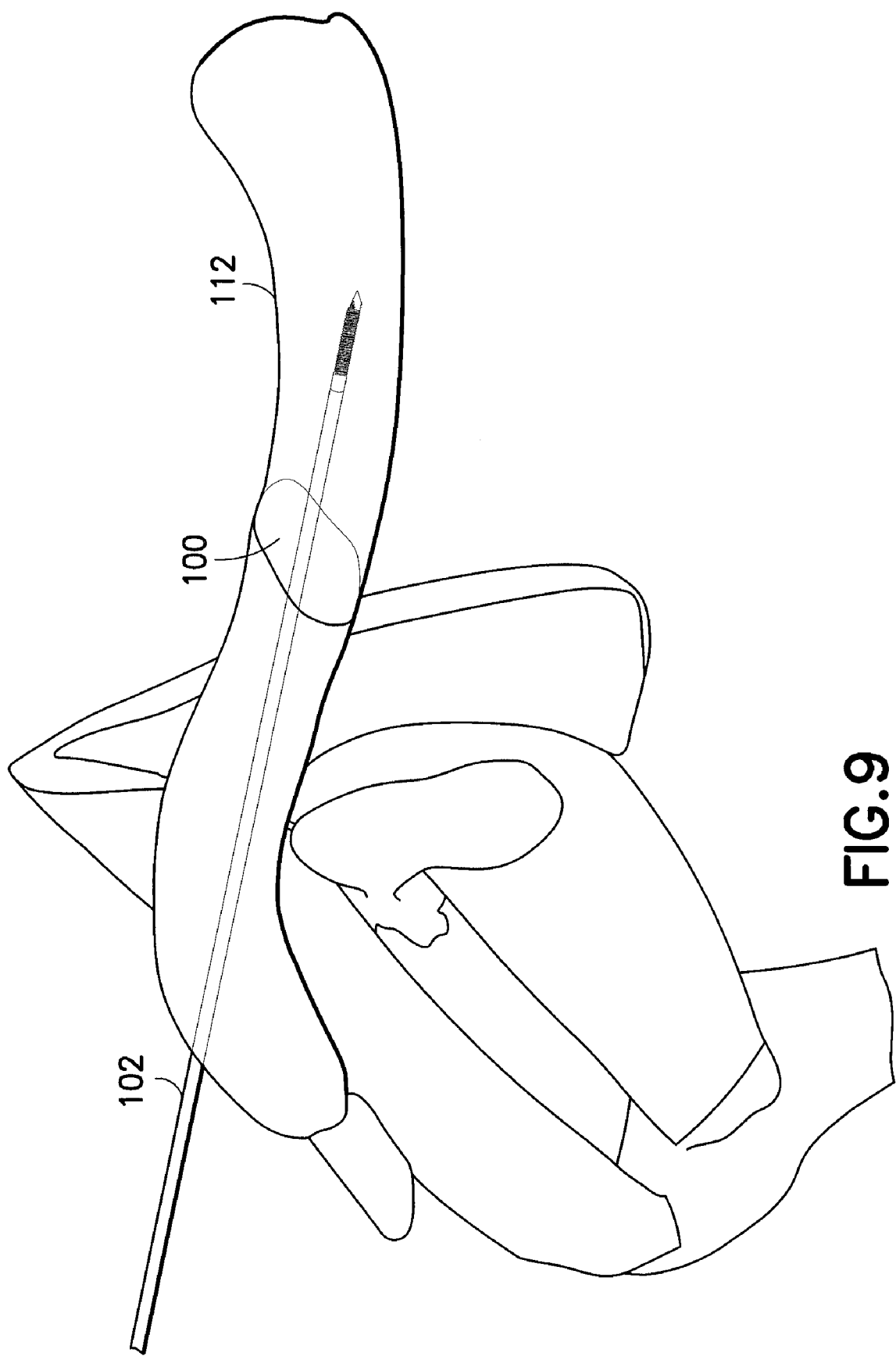
Figure 10:
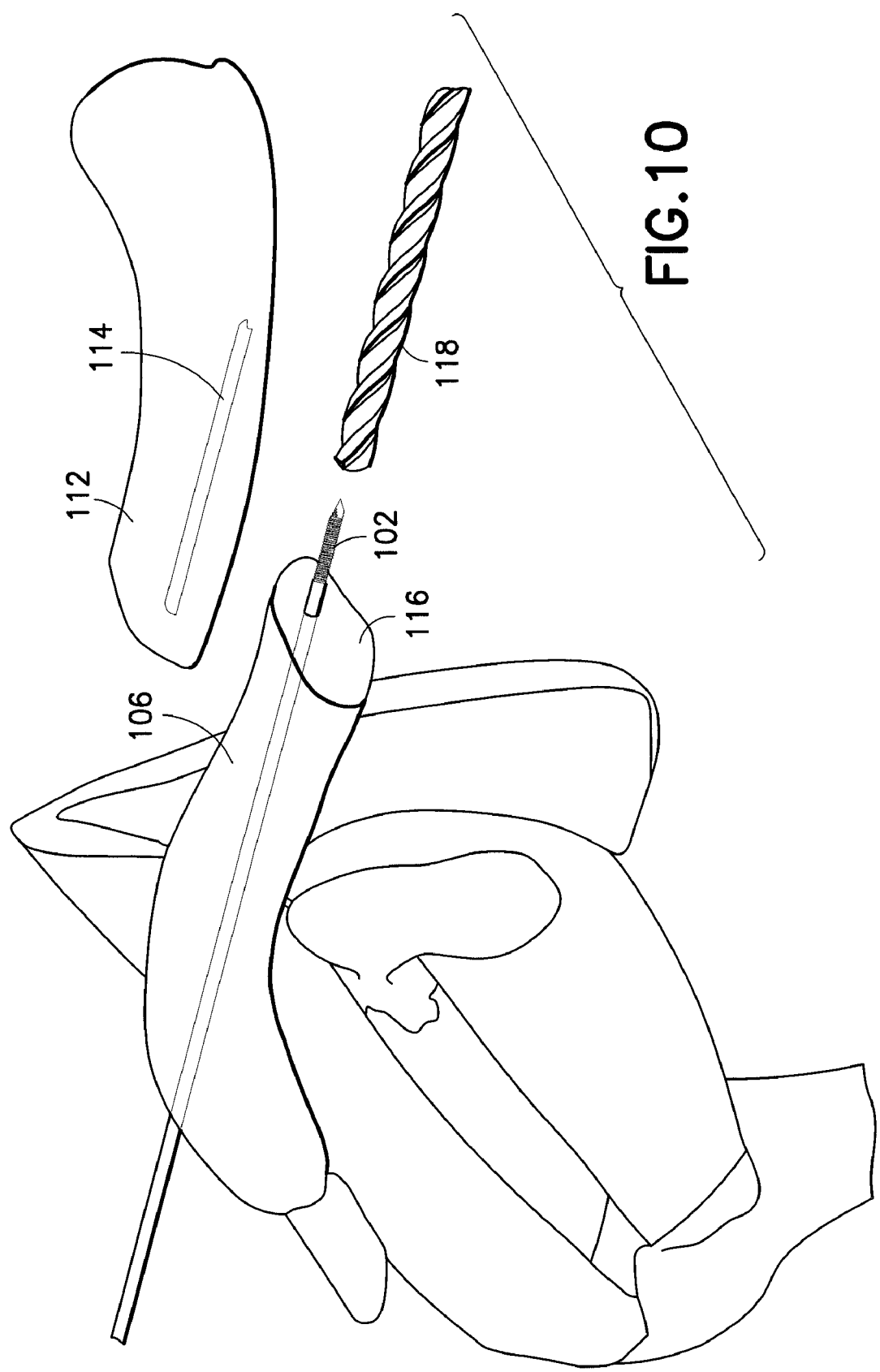

In view of the above descriptions of the nail and jig, a preferred method for positioning and coupling the clavicle nail inside the intramedullary canal of a fractured clavicle according to the invention is now described. Turning now to FIG. 6, an anterior incision is made to expose the clavicle fracture 100. Such incision is preferably similar to that used in the procedure for insertion of the Rockwood Clavicle Pin, available from DePuy. Referring to FIG. 7, once the fracture is exposed, a first K-wire 102 (or other small diameter instrument such as a drill bit) with two pointed ends 104, 105 (FIG. 8), is advanced through the lateral fragment 106 from the medial side (fracture side) 108. The first K-wire 102 is advanced until a pilot hole is formed all the way through the lateral fragment 106 and until the leading end (lateral tip 104) penetrates through the skin surface. Referring to FIG. 8, a motorized drill (not shown) is attached to the lateral tip 104 and operated to retract the first K-wire 102 laterally until the trailing end (medial tip 105) of the first K-wire is flush with the fracture 100 or slightly retracted within the lateral fragment 106. The sharp lateral tip 104 is preferably then removed with a cutter to leave a blunter end to avoid injury to the surgical staff. The fracture 100 is then reduced to the position shown in FIG. 9. Referring to FIGS. 9 and 10, the motorized drill is re-attached to the first K-wire 102 to advance the first K-wire approximately, and preferably at least, half the length of the nail 10, into the medial bone fragment 112 to make a pilot hole 114 on the fracture side of the medial fragment. The first K-wire 102 is again retracted to expose the fracture surface 116 of the lateral fragment and permit the lateral and medial fragments 106, 112 to be separated.

Figure 11:
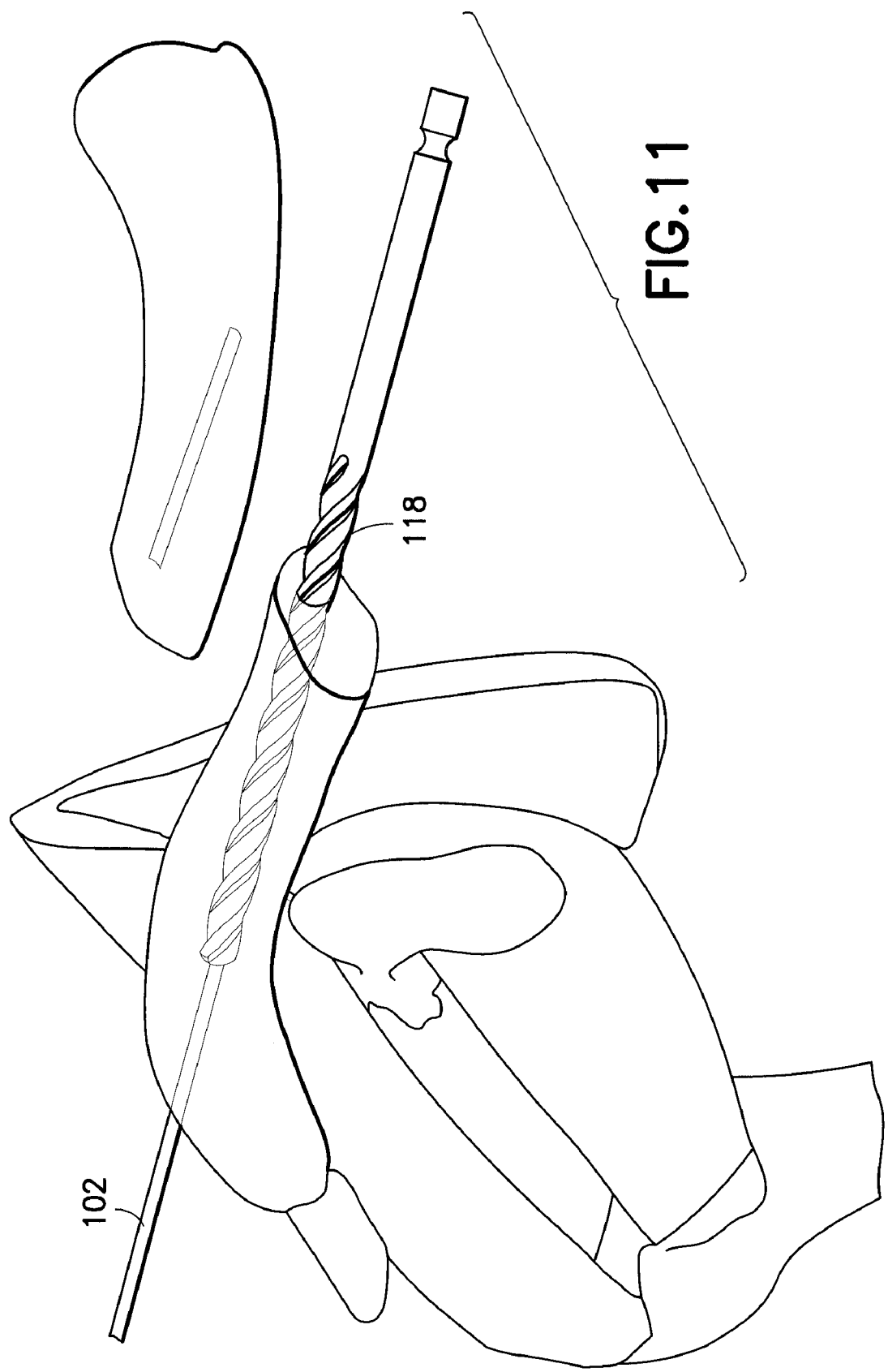
Figure 12:
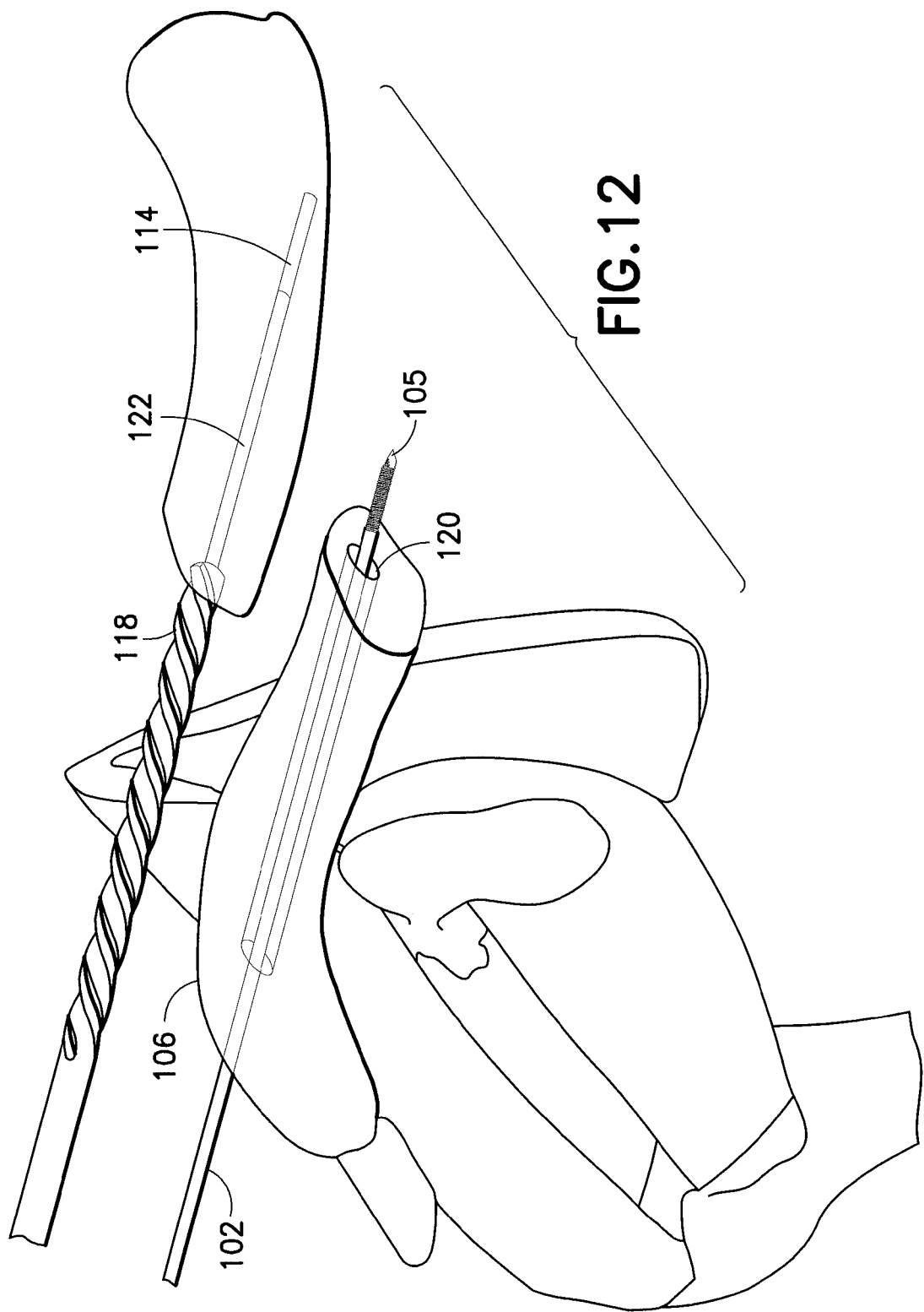

Referring to FIGS. 10 and 11, a cannulated drill bit 118 is then advanced over the first K-wire 102 (using the first K-wire as a guide) to create a lateral fragment canal 120, shown in FIG. 12. The canal length is preferably approximately the same length as the nail 10, may be slightly longer in length, but should not be shorter in length as such will impede reduction of the fracture after nail placement, as will become apparent from the description below. Referring to FIG. 12, the cannulated drill bit 118 is removed, but the first K-wire 102 is left within the lateral fragment 106, with its medial tip 105 extending or extendable from the fracture site.

Figure 13:
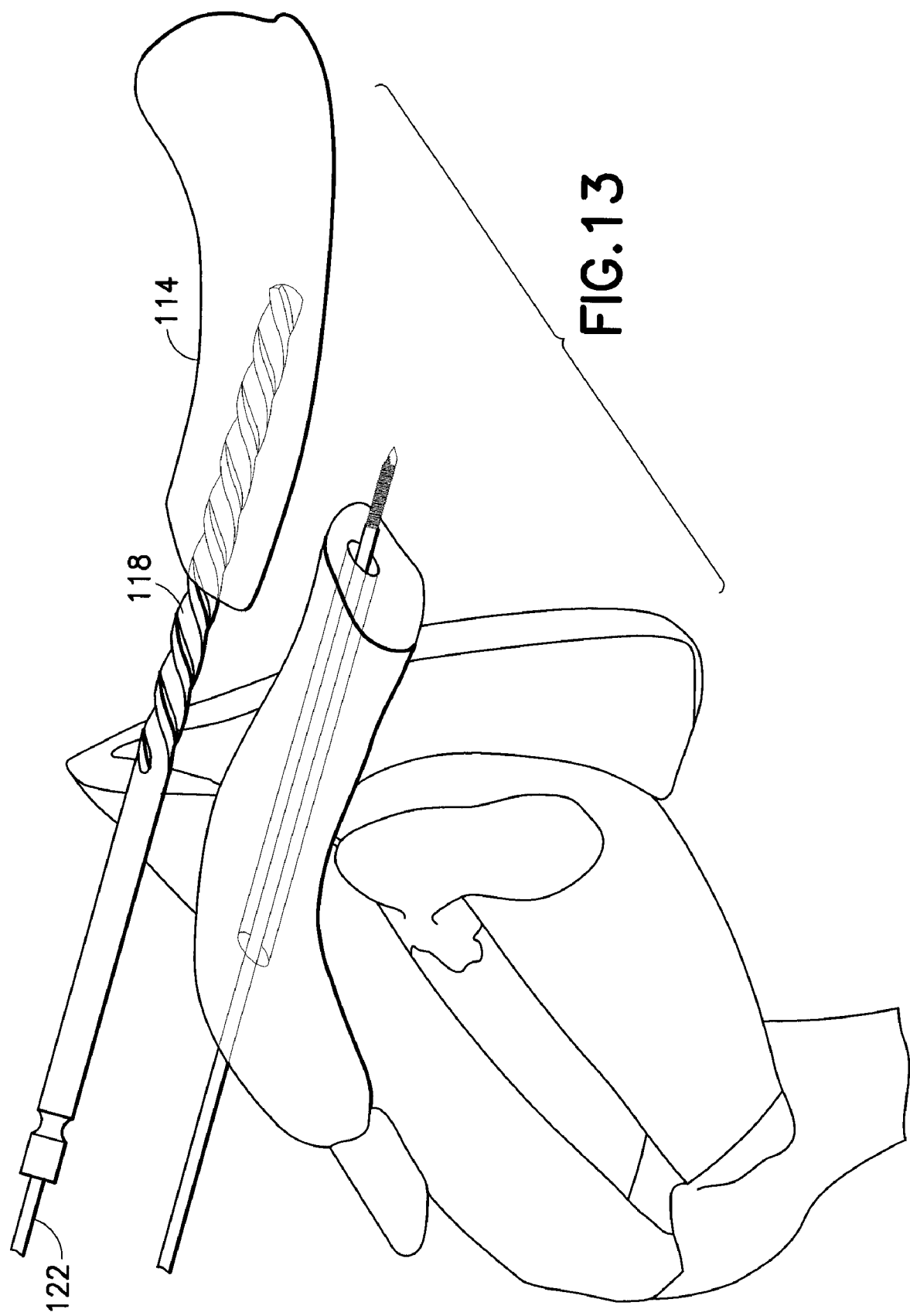

Referring to FIGS. 12 and 13, a second K-wire 122 is inserted into the medial fragment pilot hole 114. The cannulated drill bit 118 is then advanced over the second K-wire 122 to drill a medial fragment canal 124, shown in FIG. 14. The depth of the medial fragment canal 124 is preferably approximately one-half the length of the nail 10 but can be longer or slightly shorter. The cannulated drill bit 118 and second K-wire 122 are then removed from the medial fragment 114.

Figure 14:
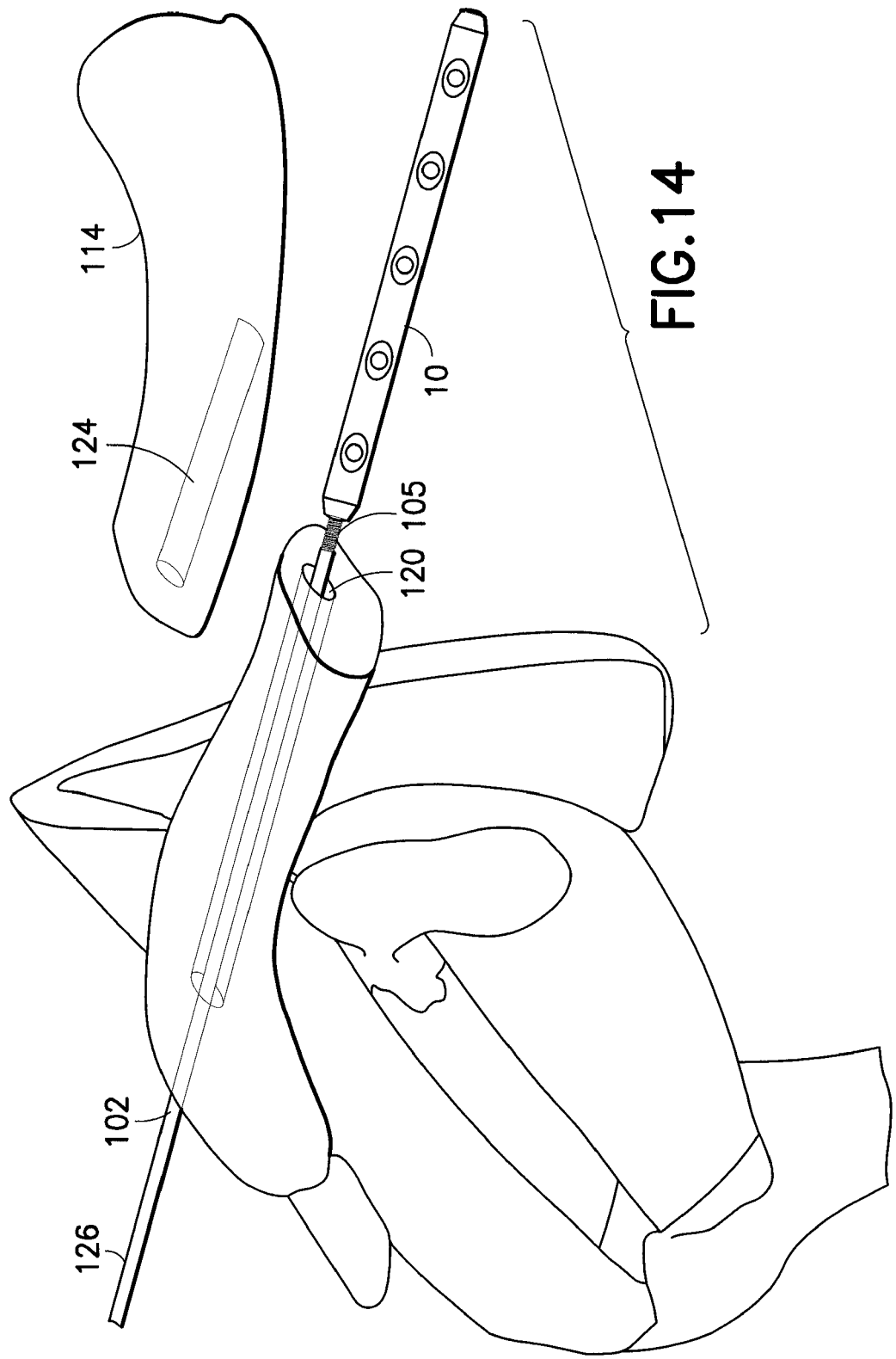
Figure 15:
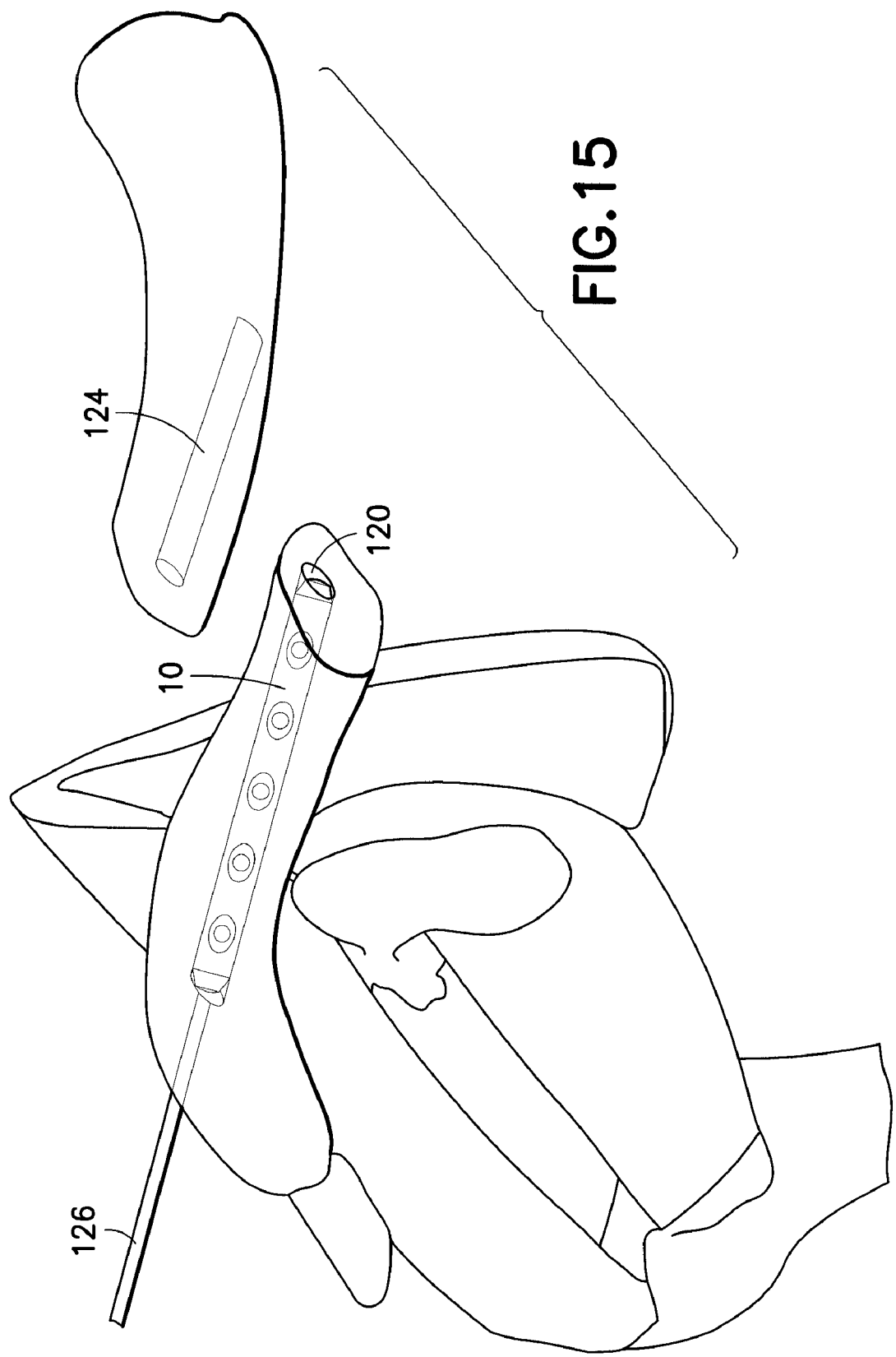
Figure 16:
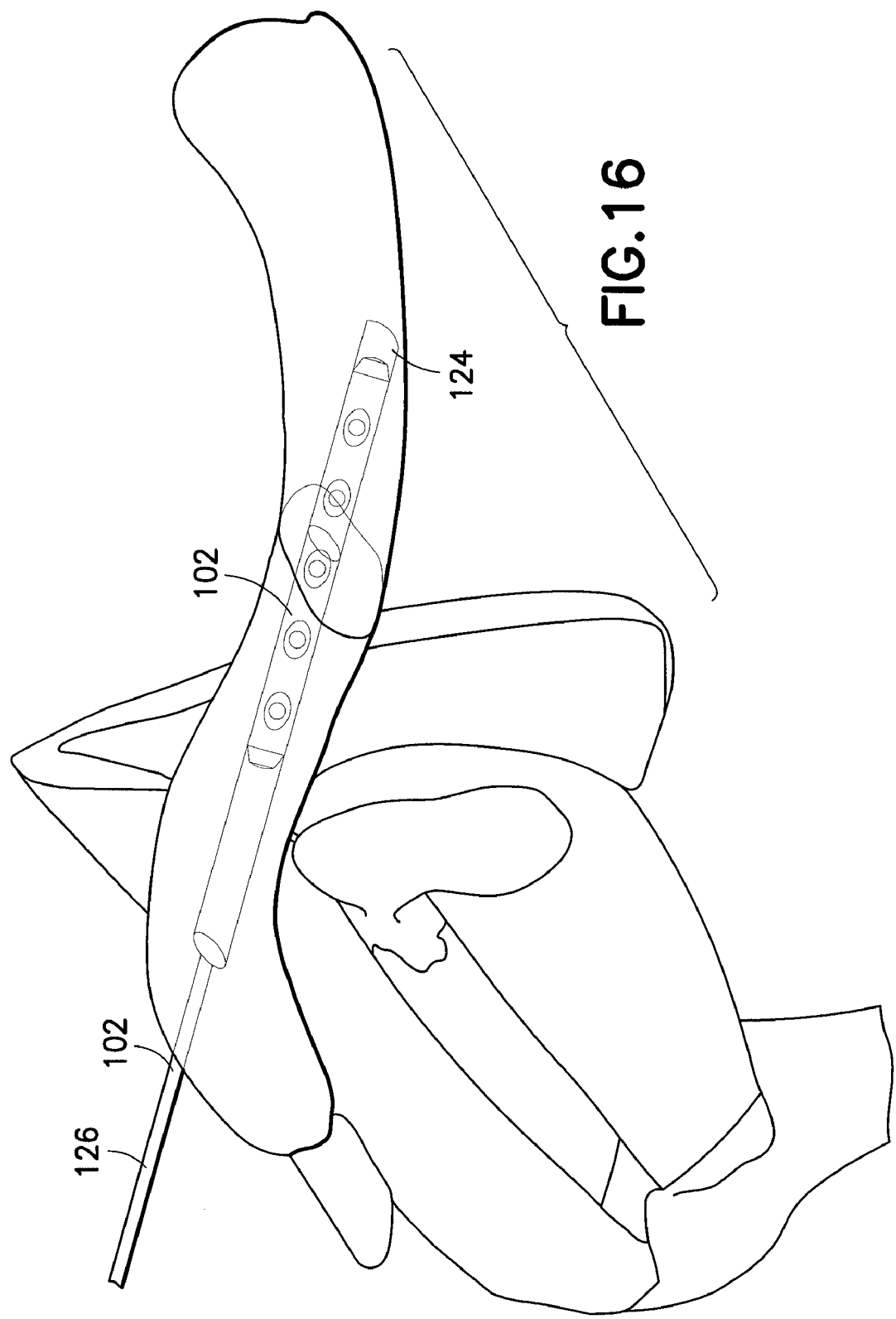

Still referring to FIG. 14, the medial end 105 of the first K-wire 102 is then removably coupled to an end of a nail 10. In a preferred embodiment, the medial end 105 of the first K-wire is threaded, and a threaded coupling is made between the medial end 105 and a threaded bore 30 of the nail 10 (FIG. 3). Other couplings are possible, particularly when using different embodiments of a clavicle nail. Referring to FIG. 15, a portion 126 of the first K-wire 102 exposed through the skin is pulled to draw the nail 10 into the lateral fragment canal 120. Referring to FIG. 16, the fracture is again aligned and exposed portion 126 of the first K-wire 102 is manipulated to advance the nail 10 medially into the medial fragment canal 124.

Figure 17:
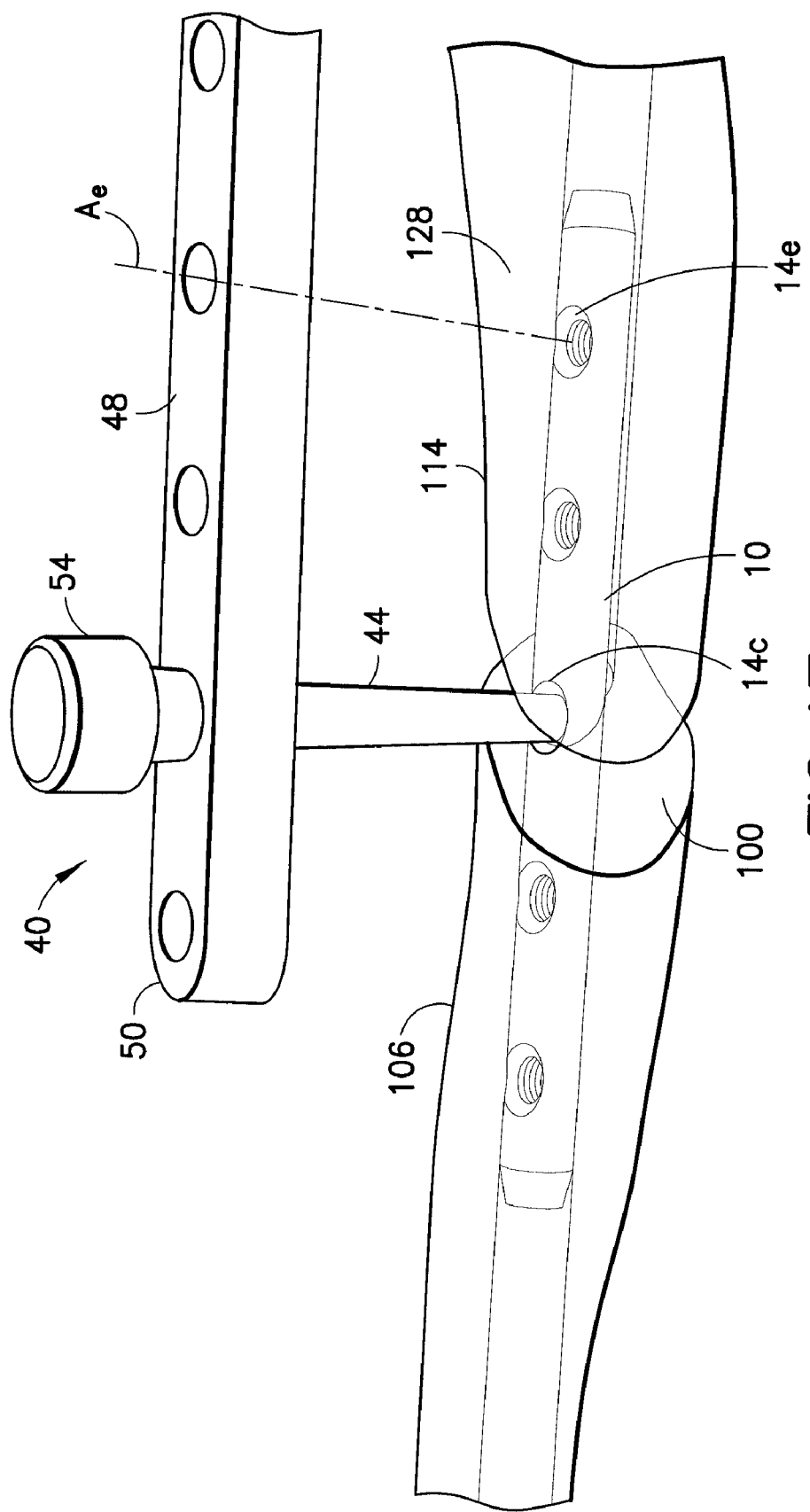
Figure 18:
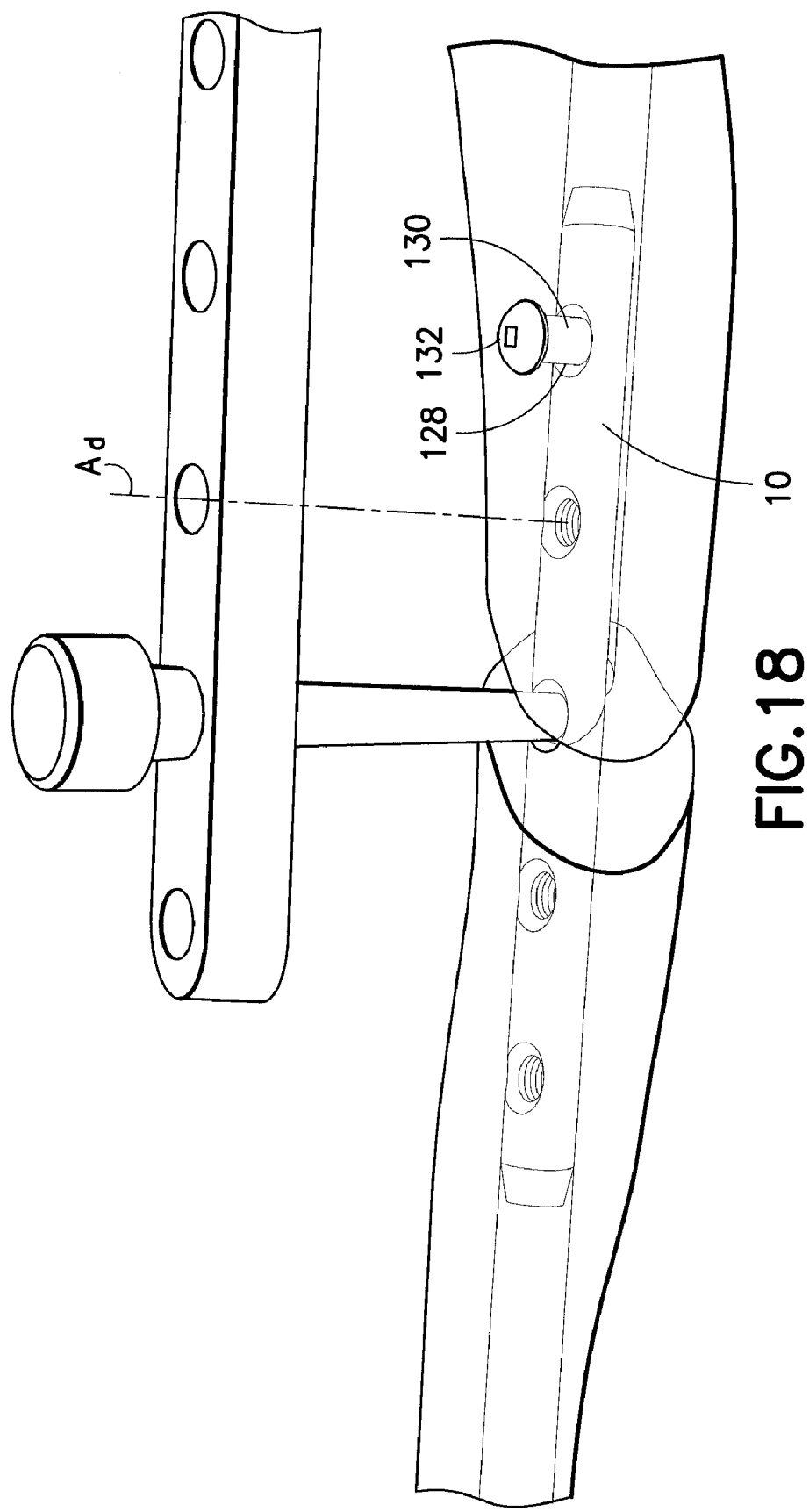

Turning now to FIG. 17, the jig 40 is then arranged relative to the nail 10 such that the longer portion 48 extends over the medial fragment 114 and nail portion situated therein, and the offset tube 44 is passed through the fracture site 100 and coupled to the central jig hole 14c of the nail 10 with the locking screw 54. The jig is oriented with the longer guide portion 48 over the medial fragment 114. A drill guide 62 (FIG. 4) is inserted through the guide hole situated over the first medial hole 14e in the nail 10, and a hole is drilled into the near cortex 128 of the clavicle bone with a 2.8 mm drill bit (in alignment with axis $A_e$). The drill guide and bit are removed. Referring to FIG. 18, using a driver, a unicortical screw 130 is advanced through the drilled hole and threadably engaged into the nail 10 until the near cortex bone 128 is compressed between the nail 10 and screw head 132.

Figure 19:
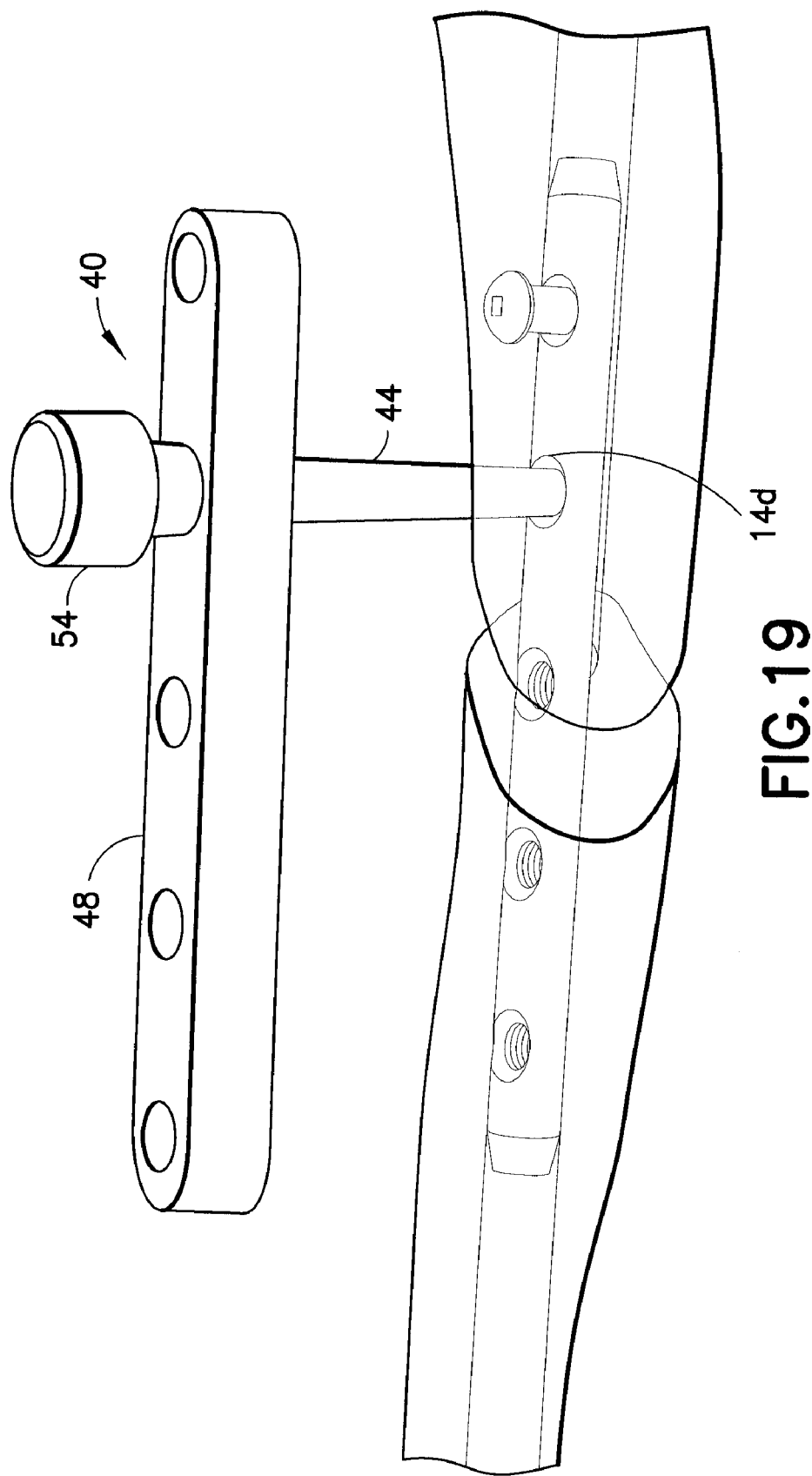

Referring to FIGS. 18 and 19, the drill guide is then inserted through the guide hole situated over the second medial hole 14d in the nail, and a hole is drilled into the near cortex in alignment with axis $A_d$. The drill guide and bit are removed. Referring to FIG. 19, the jig 40 is decoupled from the nail and the offset tube 44 is inserted into the previously drilled hole (along axis $A_d$) and the second medial hole 14d, with the larger portion 48 of the guide plate 46 now oriented toward the lateral direction. The jig is locked at this location and in this orientation with the screw 54.

Figure 20:
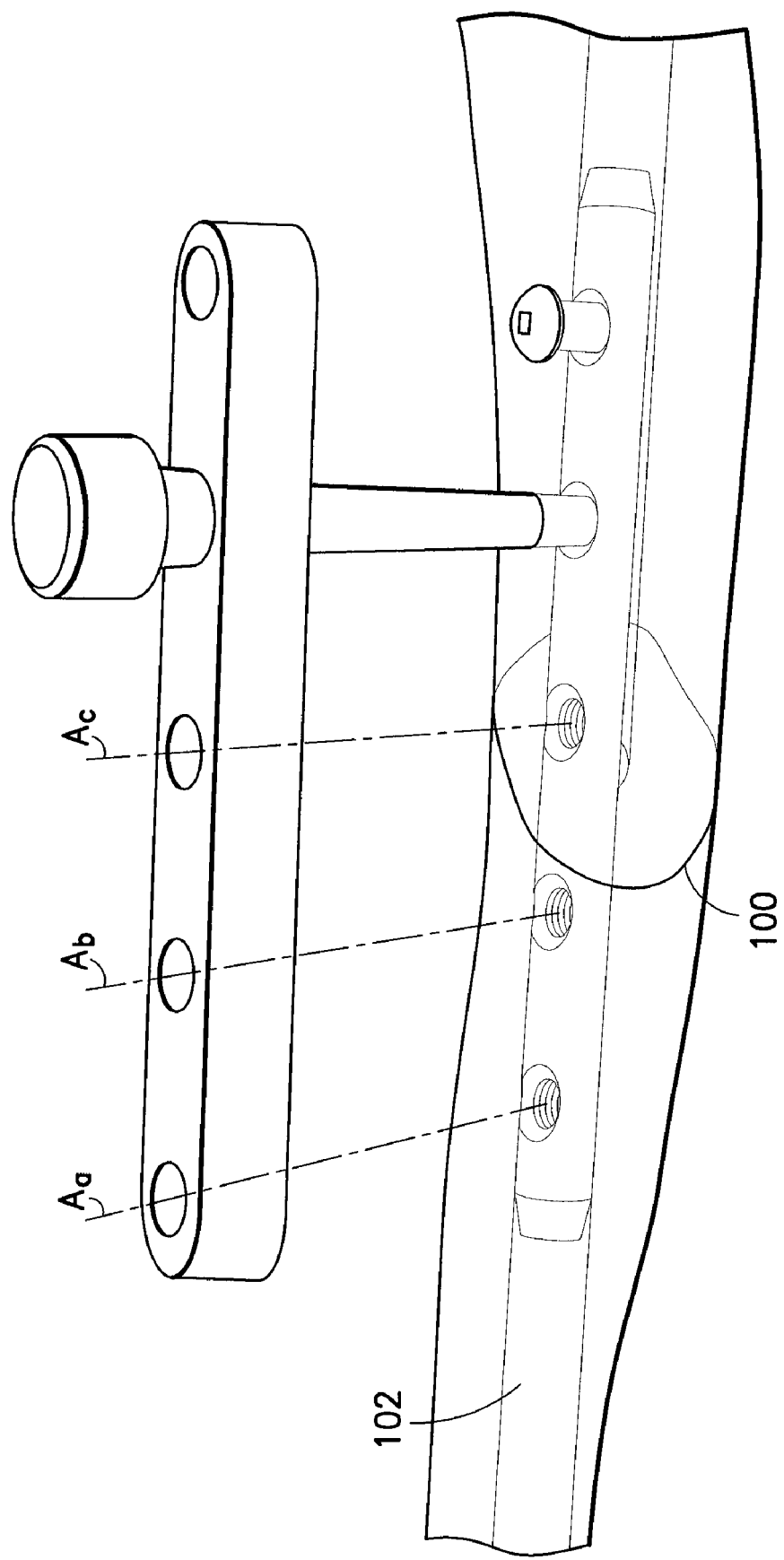
Figure 21:
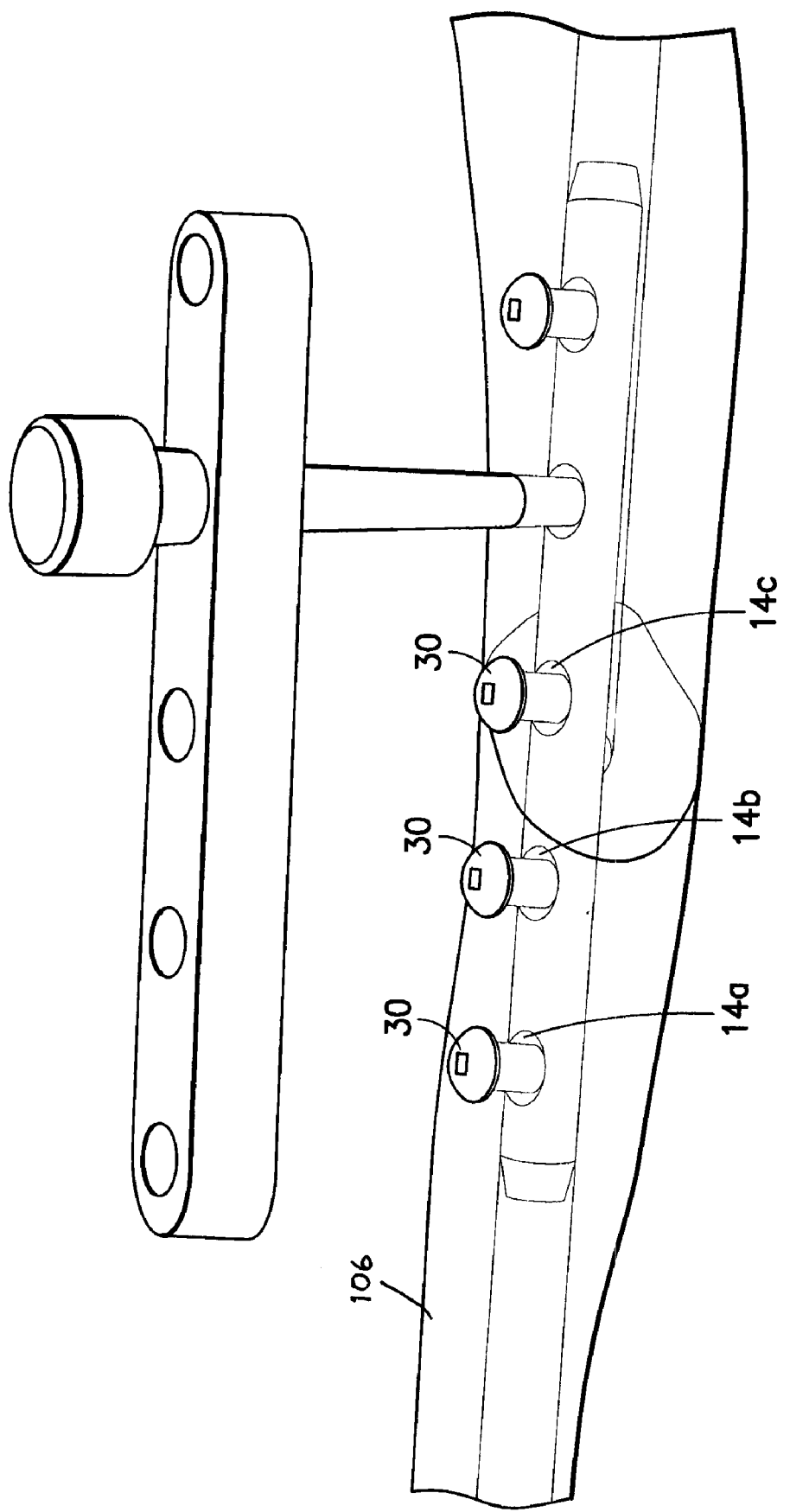
Figure 22:
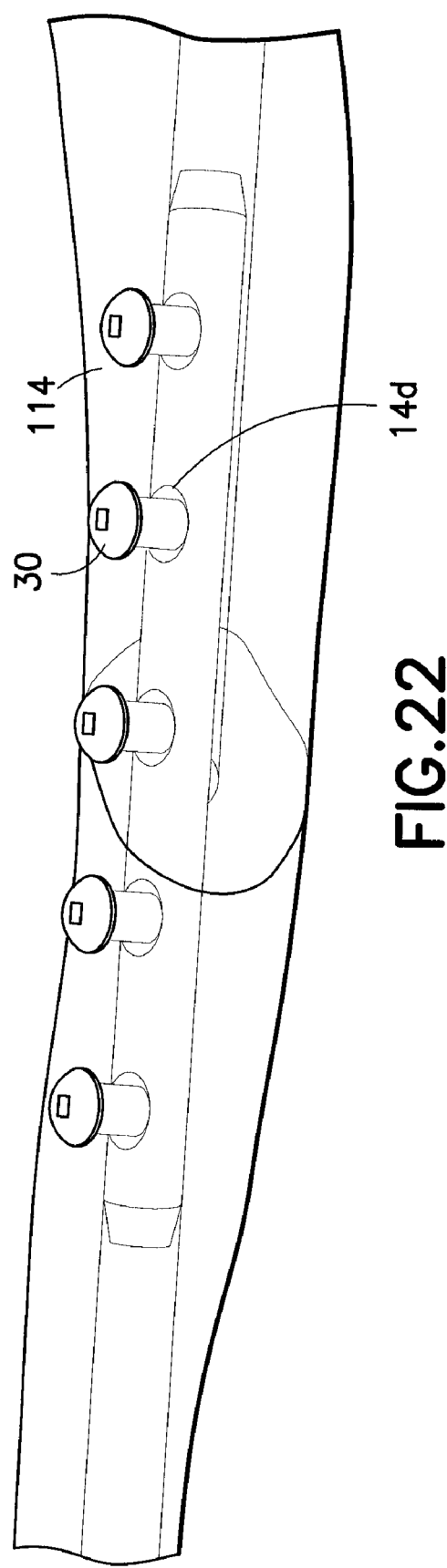

Turning to FIGS. 20 and 21, the exposed portion 126 (FIG. 16) of the first K-wire 102 is then pulled to reduce the fracture 100. Using the drill guide and drill bit, holes are then drilled along axes $A_a$, $A_b$, $A_c$ for screw holes 14a, 14b, 14c for the portion of the nail extending in the lateral fragment 106 and corresponding unicortical screws 30 are implanted (FIG. 21). Referring to FIG. 22, the jig 40 is then removed and a final unicortical screw 30 is implanted in the medial fragment 114 in the available screw hole 14d. The first K-wire 102 is then rotated relative to the nail to remove the nail 10.

From the above, it can be summarized that the procedure of the invention includes (i) using an instrument to create a pilot hole extending longitudinally through the medullary canal of the lateral and medial fragments of the fractured clavicle while the fragments are reduced, or held in an approximate healing alignment, (ii) enlarging a medial portion of the pilot hole in the lateral fragment and a lateral portion of the pilot hole in the medial fragment, wherein such enlarged portions are together sized for receiving the clavicle nail, (iii) attaching the lateral end of the clavicle nail to the instrument, (iv) manipulating the instrument such that substantially the entire length of the clavicle nail is positioned inside of the lateral fragment, (v) aligning the lateral and medial fragments longitudinally, and (vi) manipulating the instrument such that portions of the clavicle nail are positioned within the lateral and medial fragments. It is preferable that approximately half of the length of the nail (i.e., within ± ten percent of the length) be provided within each of the lateral and medial fragments.

In accord with other aspects of the method of the invention, once the nail is so positioned within the lateral and medial fragments, the nail is secured to the lateral and medial fragments. In summary, the preferred method for securing the nail includes (i) preferably securing a jig to the nail between the lateral and medial fragments, (ii) drilling holes in the bone in alignment with screw holes on the medial side of the fracture, (iii) securing the nail to the clavicle bone on the medial side of the fracture, (iv) preferably securing the jig to the nail on the medial side of the fracture, (v) reducing the fracture, preferably by applying a lateral force to the nail, (vi) drilling holes in the clavicle bone in alignment with screw holes on the lateral side of the fracture, and (vii) securing the nail to the clavicle bone on the lateral side of the fracture. It is within the scope of the invention to secure the nail to the clavicle bone with a jig different than the one described and even without the use of a jig.

Figure 23:
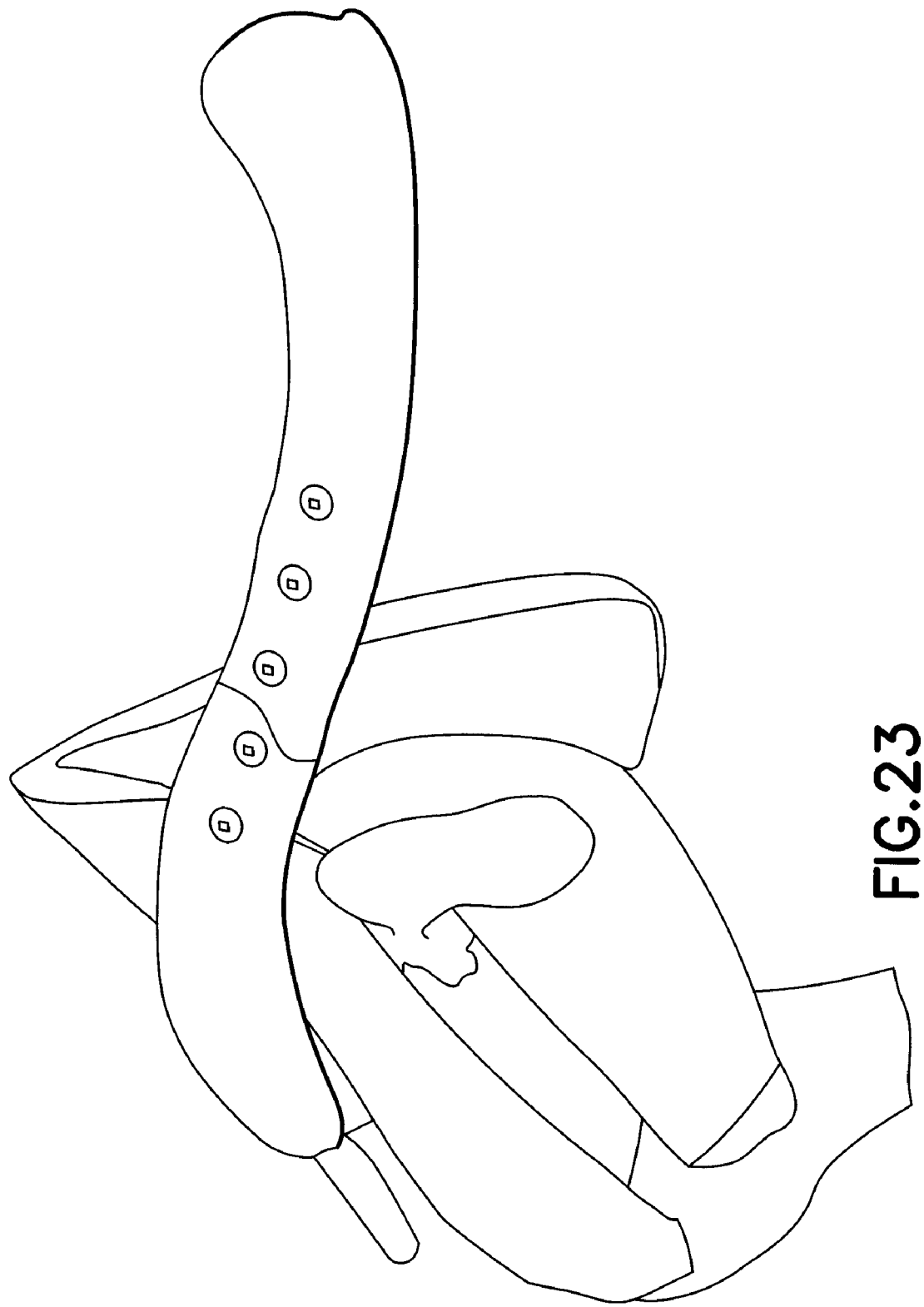

The method enables implantation of a clavicle nail in a manner that provides fractured clavicle fixation with both pin and nail advantages; i.e., minimal soft tissue stripping of the clavicle, reduced postoperative pain, and faster healing. In addition, referring to FIG. 23, the method provides for excellent fracture reduction, immobilization and support of the fracture, and minimal protrusion of the implant above the clavicle surface.

There have been described and illustrated herein several embodiments of an endosteal nail and a method of stabilizing a fracture with the nail. While particular embodiments of the invention have been described, it is not intended that the invention be limited thereto, as it is intended that the invention be as broad in scope as the art will allow and that the specification be read likewise. Thus, while the method has been described with respect to clavicle fixation, it is recognized that it may also be used to stabilize fractures of other bones. In addition, while a particular orthopedic nail is shown and described with respect to practicing the method of the invention, it is appreciated that other embodiments of a nail may so be used. For example, and not by way of limitation, the nail used in the method may have a different number of screw holes than described, differently shaped socket than described for locking relative to the jig, and not have the described symmetry. It will therefore be appreciated by those skilled in the art that yet other modifications could be made to the provided invention without deviating from its spirit and scope as claimed.

What is claimed is:

1. A method of treating a fracture of a clavicle bone having lateral and medial fragments, comprising:
    a) providing a first instrument having a first end and a second end;
    b) drilling with the first instrument in a first longitudinal direction from the medial side of the fracture and into a medullary canal of the lateral fragment such that the first instrument creates a pilot hole in the lateral fragment and the first end of the first instrument penetrates the skin surface;
    c) then retracting the first end of the first instrument from the lateral fragment in the first longitudinal direction until the second end is flush with the fracture or retracted within the lateral fragment;
    d) then, with the second end of the first instrument in the lateral fragment, orienting the lateral and medial fragments in an alignment of a reduced fracture;
    e) then advancing the second end of the first instrument in a second longitudinal direction opposite the first direction from the lateral fragment and into a medullary canal of the medial fragment to create a pilot hole in the medial fragment;
    f) enlarging a medial portion of the pilot hole in the lateral fragment and enlarging a lateral portion of the pilot hole in the medial fragment to define lateral and medial canals;
    g) first providing a clavicle nail;
    h) inserting substantially an entire length of the clavicle nail inside of the lateral canal of the lateral fragment;
    i) aligning the lateral and medial fragments; and
    j) second providing portions of the nail within each of the lateral and medial fragments.

2. A method according to claim 1, wherein:
said first instrument is a K-wire.

3. A method according to claim 1, wherein:
said first instrument is a K-wire, and said enlarging the medial portion of the pilot hole in the lateral fragment includes advancing a cannulated drill over the first instrument.

4. A method according to claim 3, wherein:
said enlarging the lateral medial portion of the pilot hole in the medial fragment includes providing a second instrument within the pilot hole of the medial fragment and advancing a cannulated drill over the second instrument.

5. A method according to claim 1, wherein:
said inserting includes
    attaching a lateral end of the clavicle nail to an instrument extending through the lateral end of the lateral fragment and protruding through the skin of the patient and
    pulling on the instrument to draw the clavicle nail into the lateral canal of the lateral fragment.

6. A method according to claim 5, wherein:
said second providing includes manipulating the instrument such that portions of the nail are positioned within each of the lateral and medial fragments.

7. A method according to claim 6, wherein:
said second providing provides approximately half of the length of the clavicle nail within the medial fragment.

8. A method according to claim 1, wherein:
said second providing provides approximately half of the length of the clavicle nail within the medial fragment.

9. A method according to claim 1, further comprising:
securing the nail to the lateral and medial fragments, wherein said securing includes,
first drilling holes in the bone in alignment with screw holes on the medial side of the fracture,
securing the nail to the clavicle bone on the medial side of the fracture,
reducing the fracture,
second drilling holes in the clavicle bone in alignment with screw holes on the lateral side of the fracture, and
securing the nail to the clavicle bone on the lateral side of the fracture.

10. A method according to claim 9, wherein:
said securing further includes,
prior to said first drilling holes, coupling a jig to the nail between the lateral and medial fragments.

11. A method according to claim 10, wherein:
the jig includes a guide plate, and the jig is coupled to the nail in a rotationally fixed manner such that the guide plate is parallel to the nail.

12. A method according to claim 10, wherein:
said securing further includes,
prior to said second drilling holes, coupling the jig to the nail on the medial side of the fracture.

13. A method of treating a fracture of a bone having first and second elongate fragments, comprising:
a) providing a first instrument having a first end and a second end;
b) drilling with the first instrument from the fracture and into a medullary canal of the first fragment such that the first instrument creates a pilot hole in the first fragment and the first end of the first instrument penetrates a skin surface at a longitudinal end of the first fragment;
c) then retracting the first end of the instrument from the first fragment in a first direction until the second end of the instrument is flush with the fracture or retracted within the first fragment;
d) then orienting the first and second fragments in an alignment of a reduced fracture;
e) then advancing the second end of the first instrument in a second direction opposite the first direction and into the second fragment to create a pilot hole in a medullary canal of the second fragment;
f) enlarging a portion of the pilot hole in each of the first and second fragments to define first and second canals to accommodate an orthopedic nail having a diameter greater than the diameter of the pilot hole;
g) first providing an orthopedic nail;
h) inserting substantially an entire length of the nail inside of the first canal of the first fragment;
i) aligning the first and second fragments; and
j) second providing portions of the nail within each of the first and second fragments.

14. A method according to claim 13, wherein:
said first instrument is a K-wire.

15. A method according to claim 13, wherein:
said pilot hole is created with a first instrument, and said enlarging the fracture side portion of the pilot hole in the first fragment includes advancing a cannulated drill over the first instrument.

16. A method according to claim 15, wherein:
said enlarging the fracture side portion of the pilot hole in the second fragment includes providing a second instrument within the pilot hole of the second fragment and advancing a cannulated drill over the second instrument.

17. A method of implanting a nail within first and second elongate fragments of a bone fracture, the nail including a longitudinal axis, a plurality of threaded screw holes transverse to the longitudinal axis, and an end, said method comprising:
a) providing a first instrument having a first end and a second end;
b) drilling with the first instrument from the fracture and into the first fragment in a first direction such that the first end of the first instrument extends through a medullary canal of the first instrument extends through the medullary canal of the first fragment and penetrates a skin surface to create a pilot hole in the first fragment;
c) then retracting the first instrument in the first direction until the second end of the instrument is flush with the fracture or retracted within the first fragment;
d) then orienting the first and second fragments in an alignment of a reduced fracture;
e) then advancing the second end of the first instrument in a second direction opposite the first direction into a medullary canal of the second fragment to create a pilot hole in the second fragment;
f) coupling the end of the nail to the second end of the first instrument and pulling on the first instrument in the first direction from the portion of the first instrument that has penetrated the skin surface to draw the nail into the first fragment; and
g) advancing screws into the threaded screw holes of the nail to secure the nail relative to the bone.

18. A method according to claim 17, further comprising:
enlarging portions of the pilot hole in each of the first and second fragments prior to drawing the nail into the first fragment with the first instrument.

19. A method according to claim 17, further comprising:
using the first instrument to advance the nail into the second fragment.

20. A method according to claim 17, wherein:
the end of the nail includes a threaded axial bore, the second end of the first instrument is threaded, and said coupling includes threading the second end of the first instrument into engagement with the end of the nail.

* * * * *

UNITED STATES PATENT AND TRADEMARK OFFICE
CERTIFICATE OF CORRECTION

| | | |
|---|---|---|
| PATENT NO. | : 7,722,611 B2 | Page 1 of 1 |
| APPLICATION NO. | : 11/682210 | |
| DATED | : May 25, 2010 | |
| INVENTOR(S) | : Cesare Cavallazzi et al. | |

It is certified that error appears in the above-identified patent and that said Letters Patent is hereby corrected as shown below:

Claim 17, Column 8, Line 25-26: Delete the words "of the first instrument extends through the medullary canal".

Signed and Sealed this
Eighth Day of May, 2012

David J. Kappos
*Director of the United States Patent and Trademark Office*